United States Patent [19]
David et al.

[11] 4,048,041
[45] Sept. 13, 1977

[54] ELECTRONIC SYSTEM FOR PROVIDING SPECIFICITY IN AN ELECTROCHEMICAL ANALYTICAL DEVICE

[75] Inventors: Donald J. David; Huel C. Tucker, both of Centerville, Ohio

[73] Assignee: The United States of America as represented by the Secretary of the Army, Washington, D.C.

[21] Appl. No.: 689,287

[22] Filed: May 24, 1976

[51] Int. Cl.² .......................................... G01N 27/48
[52] U.S. Cl. .......................... 204/195 R; 204/1 T; 204/195 H; 324/29
[58] Field of Search .............. 204/1 N, 1 K, 195 H, 204/195 R; 324/29

[56] References Cited
U.S. PATENT DOCUMENTS

| 3,420,764 | 1/1969 | Schlein | 204/195 H |
| 3,922,205 | 11/1975 | McLean et al. | 204/195 H X |

FOREIGN PATENT DOCUMENTS 1,440,371  4/1966  France ........................... 204/195 H

*Primary Examiner*—G. L. Kaplan
*Attorney, Agent, or Firm*—Nathan Edelberg; A. Victor Erkkila; Max Yarmovsky

[57] ABSTRACT

An electronic circuit is used to continuously determine the nitroglycerin concentration in a sample solution of an electrochemical monitoring cell by controlling the applied potential to a cathode electrode of a three element cell. The cathode of the electrochemical cell is maintained at a desired potential by supplying a square wave modulated negative potential signal thereto and then measuring the difference in cell current between the cathode and anode elements at the start and finish of the pulse signal with a demodulator. Current from any additional reactions that are constant or that occur above a desired reduction potential within the electrochemical cell are automatically cancelled by a gating circuit which is electrically coupled to the demodulator.

8 Claims, 4 Drawing Figures

ELECTRONIC SYSTEM FOR PROVIDING SPECIFICITY IN AN ELECTROCHEMICAL ANALYTICAL DEVICE

GOVERNMENTAL INTEREST

The invention described herein was made in the course of a contract with the Government and may be manufactured, used and licensed by or for the Government for governmental purposes without the payment to us of any royalty thereon.

BACKGROUND OF THE INVENTION

The continuous processing of nitroglycerin generally produces a waste-water stream which must be treated so that it can meet rigid pollution standards. In order to determine the effectiveness of the pollution abatement equipment, there is a need for a continuous monitoring device for measuring and monitoring the concentration of nitroglycerin in waste water before and after the pollution treatment equipment.

Prior art polargraphic devices generally apply a linear voltage ramp to a dropping mercury electrode of an electrochemical cell. These devices in some cases measure the increase in current due to an electro-oxidizable or reducible species and display this current on a sensing and/or recording type instrument. Other prior art polargraphic devices take the derivative of the resulting signal, which is generally noisy, and display the signal oscillographically. Derivative circuitry is not only noisy, but is complex, expensive and not amenable to use in a continuous monitor, although it is entirely acceptable for laboratory type instrumentation used to spot check a sample solution. Other prior art polargraphic devices ramp the applied voltage to the electrochemical cell and while pulsing the ramp voltage measure the change in cell current before and after the pulse. Some prior art polargraphs use a dropping mercury type electrode in order to provide a continually new, fresh, mercury surface with which to work. The dropping mercury type electrode is very difficult to use in a continuous monitor because of the variation in time in the dropping of the mercury from capillaries and the need for synchronization of current sensing circuitry. Use in the prior art of a stationary mercury electrode precludes renewal of electrode surface. In the aforementioned prior art polargraphic device, the stationary mercury electrode surface frequently becomes fouled cathode various species and byproducts of the electro-oxidation-reduction start as the applied voltage is varied over the potential ranges of interest and often becomes unreliable and insensitive as a continuous monitor of waste water.

SUMMARY OF THE INVENTION

The present invention relates to an electronic circuit which continuously provides specificity in an electrochemical analytic device by controlling the applied potential to the working electrodes of an electrochemical cell. The present device uses a modulated negatively biased pulsed DC signal and measures the difference in cell current at the start and finish of the pulse using a demodulator with a differential amplifier circuit to give the current due only to the nitroglycerin reduction.

The present invention utilizes a three-electrode electrochemical cell which includes a mercury pool cathode, a platinum wire anode and a calomel reference electrode. Reduction of nitroglycerin, hereinafter referred to as (NG), occurs at the surface of the mercury pool cathode. The resultant current is measured between the cathode and anode.

NG reacts in a three-step sequence of two electrons per step as each of three -ONO$_2$ groups is reduced. The potentials at which these steps occur are as follows:

Reduction of First -ONO$_2$ group occurs at $-0.25V$
Reduction of Second ONO$_2$ group occurs at $-0.45V$
Reduction of Third -ONO$_2$ group occurs at $-0.75$ to $-0.8V$ The overall reaction being:

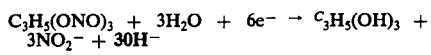

$$C_3H_5(ONO)_3 + 3H_2O + 6e^- \rightarrow C_3H_5(OH)_3 + 3NO_2^- + 3OH^-$$

The nirite ion has been found to undergo electrochemical reaction at the same potential as the NG. The electrochemical cell in the present device reduces these interferences by passing fresh solution over the cathode surface to rinse away the reaction byproducts and by measuring the difference current between the anode and cathode when the cathode potential is rapidly changed from one level to another cyclically with a modulator-demodulator circuit.

In order to remove dissolved oxygen from the sample, since it would otherwise lead to erroneously high values of NG concentration, the oxygen is removed by continuously sparging the sample with nitrogen gas prior to introduction into the chemical cell.

An object of the present invention is to provide an electronic system which gives specificity to a continuous monitoring electrochemical analytic system.

Another object of the present invention is to provide an electronic system for continuously monitoring for trace quantities of reducible or oxidizable species, simply and inexpensively while the species is in solution.

A further object of the present invention is to provide an electronic system for a continuous monitoring electrochemical cell which is designed to partially eliminate the cell current due to species other than nitroglycerin.

For a better understanding of the present invention, together with other and further objects thereof, reference is made to the following descriptions taken in connection with the accompanying drawings.

DESCRIPTION OF THE PREFERRED EMBODIMENT

In order to quantitatively reduce nitroglycerin one must hold the cathode potential of an electrochemical cell slightly more negative than $-0.8$ volts with respect to the NG-containing solution near the cathode surface.

However, if the cathode is held too negative, electrolysis of the solvent is possible. Since all species in solution which reduce at potentials more positive than −0.8 volts will react, the resultant current measured by conventional means cannot be differentiated from that due only to the nitroglycerin concentration.

Figure 1:
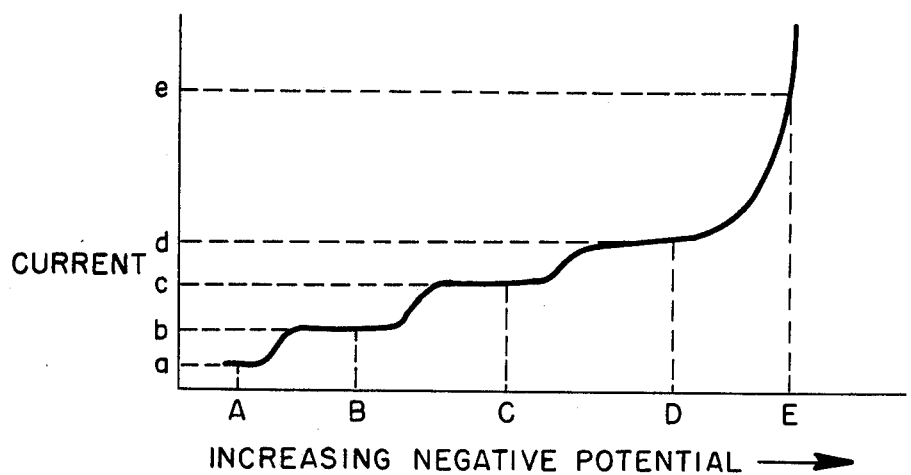
FIG. 1 is a current versus potential plot for a species which reduces in three steps.

Referring now to FIG. 1 we see a current versus potential plot taken by a conventional nitroglycerin analyzer, of a solution containing nitroglycerin, having a mercury pool cathode, a platinum wire anode, and a calomel reference electrode. A solution containing a single species such as NG having three reduction steps at three different potentials will exhibit a current rise which is the same since all steps involve the transfer of two electrons. Such solutions can be analyzed by derivative circuits; however, since derivative circuitry is inherently noisy, complex, expensive, and although it is acceptable for laboratory instrumentation, it is not amenable to use in a continuous monitor.

Figure 2:
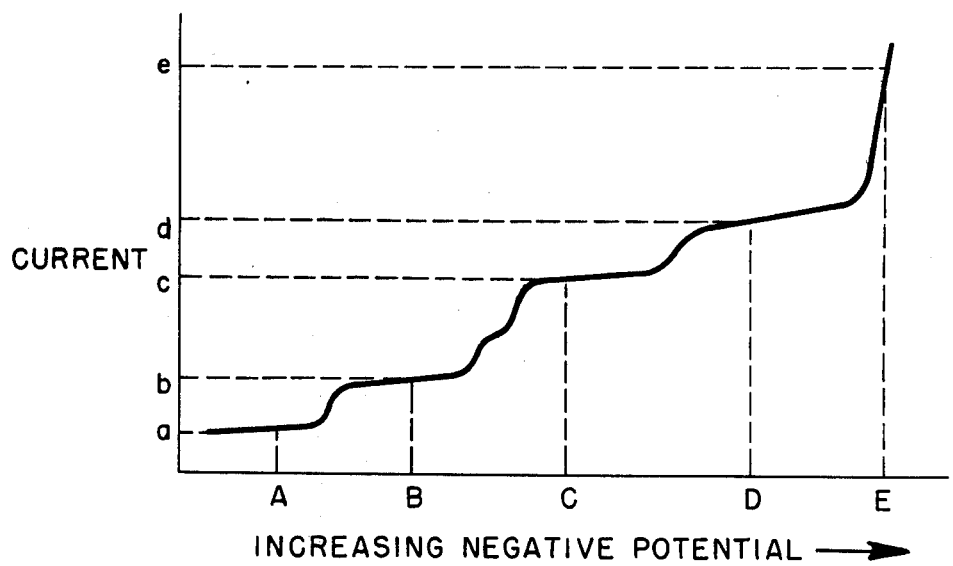
FIG. 2 is a current versus potential plot for nitroglycerin and an interfering species.
Figure 3:
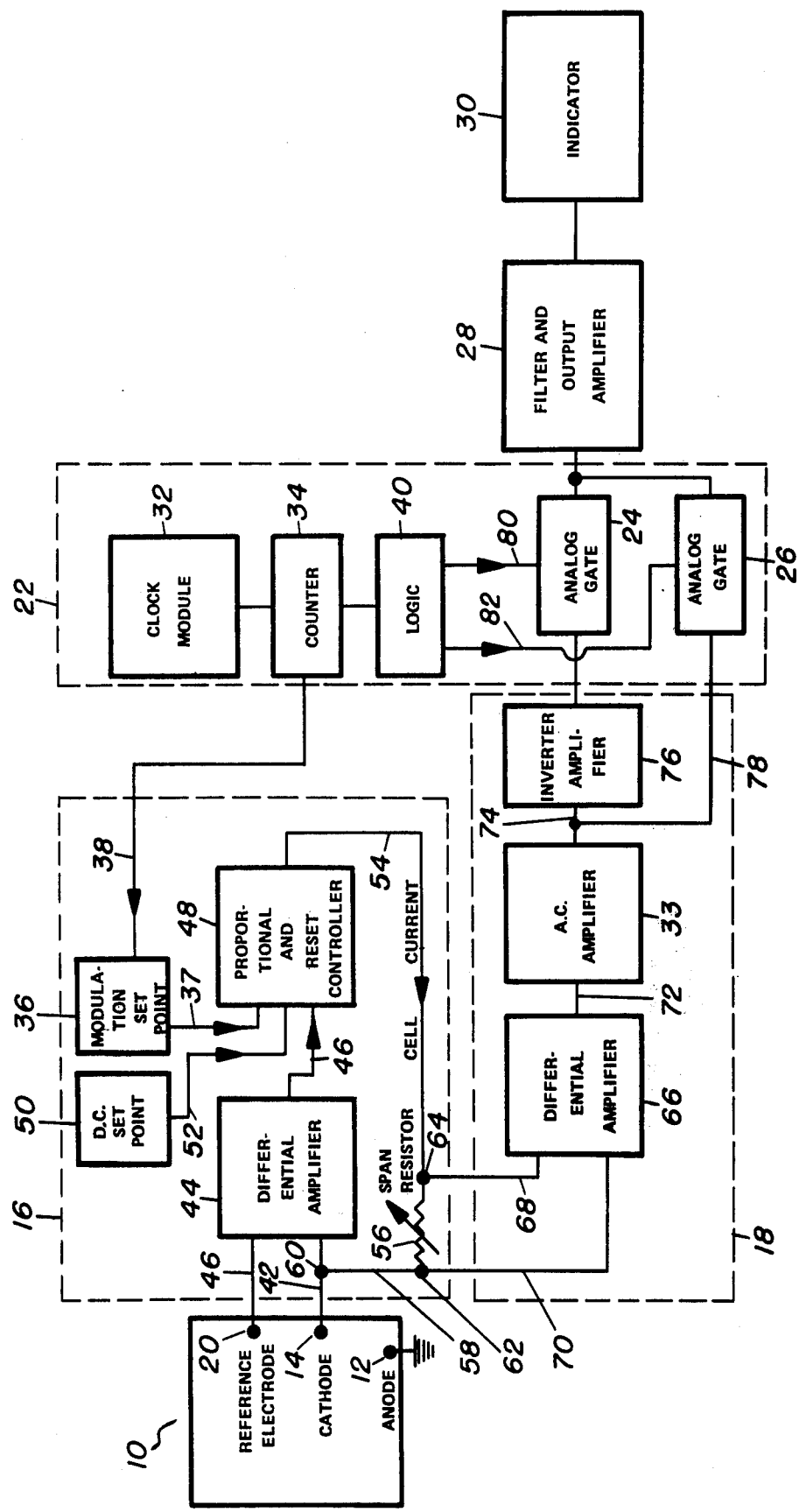
FIG. 3 is a block diagram of the modulator-demodulator electronics used to continuously measure the concentration of nitroglycerin in the solution contain in an electrochemical cell.
Figure 4:
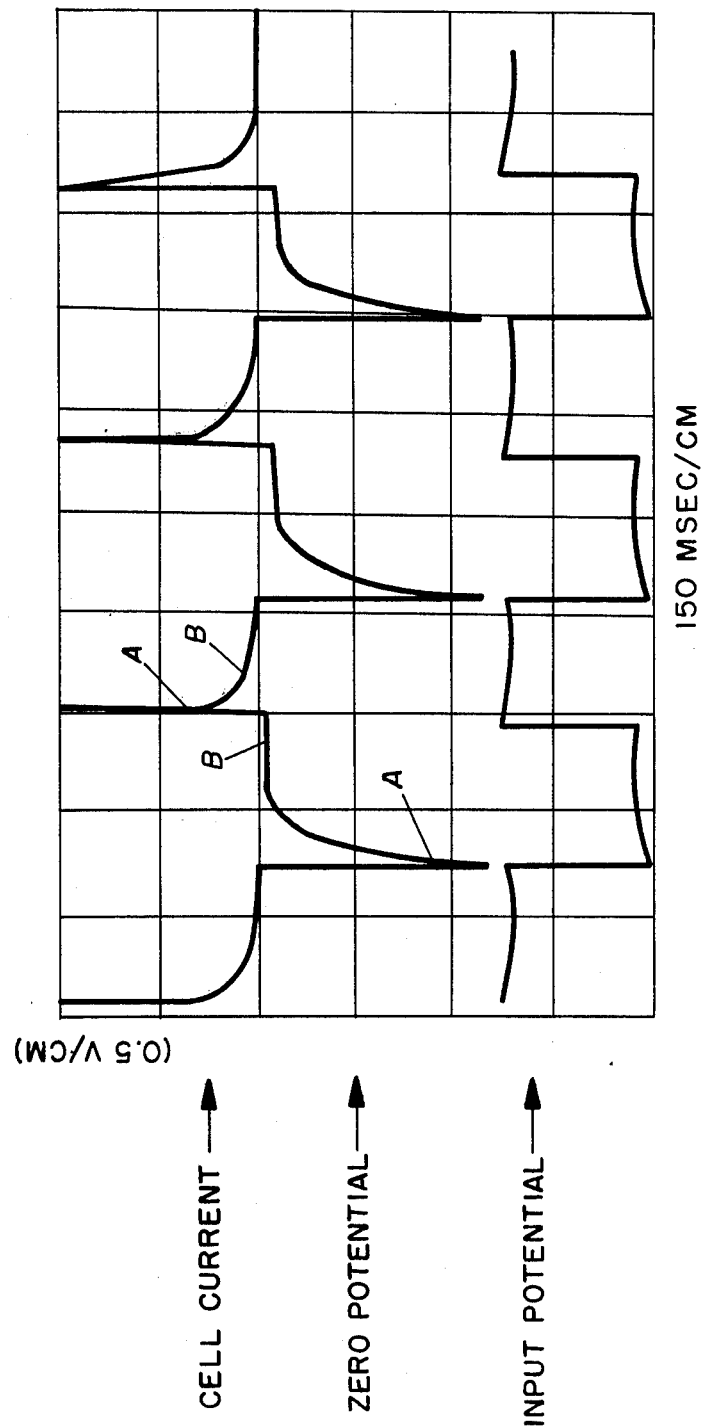
FIG. 4 are oscilloscope traces of a pulsed input potential from a modulator applied to the working electrodes of an electrochemical cell and the corresponding reduction current between the cathode and anode elements of the electrochemical cell.

Referring now to FIG. 2, a plot of current versus potential is shown for a nitroglycerin analyzer using a three element electrochemical cell having a flow system which supplies fresh solution which continually bathes the cathode. The NG solution in this instance is one which has an interfering species therein which reduces at a potential near the second $-ONO_2$ group of NG. The differential between currents $d$ and $a$ in FIG. 2 is due to the NG and the undesired species. In order to measure the NG specifically and eliminate currents due to interfering species the cathode potential in the present invention is momentarily held, at potentials D and C or at B and A while the difference current is measured. In either case the current sensitivity is only one-third as great because only two-sixths of the total electron charge is measured; however, by this method the current due to an interfering species may be eliminated. The NG analyzer shown in block diagram in FIG. 3 operates as described supra by measuring the difference current in the electrochemical cell 10 between a grounded anode 12, and a negatively pulsed cathode 14 whose potential is rapidly changed from one level to another and back again repeatedly by a modulator circuit incorporated within dash line box 16. The difference current is measured by a demodulator circuit incorporated within dash line box 18 in such manner that the current sensed is due only to NG reduction and not of an interfering species. The cathode 14 is held at a negative potential with respect to the NG-containing solution near its surface and not with respect to the anode 12 which is in integral part of the reduction current loop. A saturated calomel reference electrode 20 is positioned near the cathode surface to monitor the potential between the cathode 14 and the nearby solution. Since the saturated calomel reference electrode 20 draws essentially no current, no error potentials are generated due to IR drops, back EMF, or polarization effect. However, since the saturated calomel electrode 20 itself has a potential of +0.242 volts under standard conditions, this is taken into account when measuring the cathode-to-solution (reference electrode) potential. Since there is a relatively large current flow between the cathode and anode, the potential between these electrodes fluctuates markedly as the bulk solution composition changes, as oxidation and other anode side reactions occur, and as the electrodes are polarized and capacitively charged and discharged when the potential is cyclically varied by the modulator circuitry 16. FIG. 4 shows the oscillographic track of a pulsed input negative potential from the modulator 16 on the lower half of the drawing and a corresponding oscillographic reduction current trace of the current flowing between the cathode 14 and the anode 12 on the upper half of the drawing. As a step change in potential occurs on the cathode, a large current spike due to capacitive effects and polarization of the electrodes occurs. The large current spikes. indicated on FIG. 4 by the regions marked "A," are undesirable since they contain no useful information related to NG concentration. Very evident in the cell current wave form in the upper half of the oscilloscope trace is an AC component as well as a DC offset. Since the difference current is of importance, the difference between the currents when the cathode potential is more negative or less negative, the first and second stages of the AC amplifier 33 of the demodulator circuit 18, shown in FIG. 3, are capacitively coupled in order to cancel the DC offset. Since large current spikes are undesirable because they contain no useful information, a gating circuit inclosed within dash line box 22 is used to control the modulator circuit 16 and demodulator circuit 18, and to trigger a pair of analog gates 24 and 26 which allow only the latter half of the AC signal, marked as region "B" in FIG. 4, to be used for further processing by an electrically coupled filter and output amplifier 28. The output signal of output amplifier 28 is used to initiate an electrically connected indicator 30 which may be a device such as a digital meter, recorder, or an alarm. The gating circuit 22 comprises an electric clock module 32 which generates a square wave 60 Hz signal pulse train. The pulse train is counted by a counter 34 which is electrically coupled to the output of clock module 32. A counter 34 provides a first 5 Hz symmetrical square wave output pulse which is electrically coupled to the input of a modulation set point circuit 36 via electrical conductor 38. In addition a second 5 Hz square wave pulse signal is delivered by counter 34 to an electrically connected logic circuit 40 which causes the logic circuit 40 to generate a first and a second delayed unsymmetrical output signal which is delivered to electrically connected analog gates 24 and 26 respectively. The first output signal is delayed by a time, Td, and the other by a time, Td + (T/ 2, where T is the period of the modulating voltage. The reference cell 10 working cathode electrode 14 is electrically connected by conductor 42 to a first input of a first differential amplifier 44. The reference cell voltage at reference electrode 20 is electrically coupled to a second input of the first differential amplifier 44 by electrical conductor 46. The cathode voltage generated at cathode terminal 14 is compared to the electrochemical cell voltage generated at reference electrode 20 by the differential amplifier 44 and the difference is amplifier by first differential amplifier 44. The output of differential amplifier 44 is electrically connected by conductor 46 to the input of a two-mode controller 48. Controller 48 having a plurality of input terminals sums the difference voltage from the output of differential amplifier 44 with the output from a DC set point voltage generated by the DC set point supply 50, and with the square wave output voltage from modulation set point supply 36, via electrical conductors 52 and 37 respectively. Controller 48 drives the reference cell cathode 14 through electrical conductor 54 and through an adjustable series resistor 56 via electrical conductor 58 which is electrically connected to electrical conductor 42 at junction point 60 such that the sum of the voltage seen by the controller 48 is zero. Thus, the cathode voltage of the cell 10 is forced to assume a value such that the difference between the cathode and reference electrode voltages is a linear function of the sum of the DC and AC set point voltages. The function of the proportional and reset controller 48 is to cause the cathode voltage of reference cell 10 to assume whatever negative potential is required to force the difference between the cathode and reference electrode potentials to match the sum of the two aforementioned set point voltages.

By driving the cathode of reference cell 10 through adjustable resistor 56 a voltage is generated across juncton points 62 and 64 which is directly proportional to the reference cell 10 cathode current. A second DC differential amplifier 66, whose input is electrically coupled to junction points 62 and 64 by electrical conductors 68 and 70 respectively, provides an output proportional to the sum of the DC and AC component voltages. The output of second differential amplifier 66 is electrically connected by conductor 72 to the input of AC amplifier 33 which provides an AC output but ignores the DC component. The output of the AC amplifier 33 is electrically connected by electrical conductor 74 to inverter-DC amplifier 76 and to the input of the second analog gate 26 by electrical conductor 78. The output of the AC amplifier 33 is inverted by a gain-of-one DC amplifier 76. The outputs of AC amplifier 33 and the DC amplifier 76 are electronically switched by analog gates 26 and 24 respectively to the input of filter and output amplifier 28 in alternate half cycles of the signal voltage generated by counter 34. The control signals for the analog gates 24 and 26 are derived from the clock module 32 and logic circuit 40 via electrical conductors 80 and 82 respectively. These control signals are delayed and shortened with respect to the modulating signal generated by the modulator circuit 16 such that gates 24 and 26 remain cut off for a relatively short period to allow substantially all the switching current transients generated in the cell 10 to decay. The DC output from the filter and output amplifier 28 is electrically connected to indicator 30 so that a reading representative of the nitroglycerin concentration may be read thereon.

In operation the DC and the modulation set point circuits 50 and 36 respectively, are non-interacting. The action of the proportional and reset controller is to cause the reference cell 10 cathode voltage to assume whatever negative potential required to force the difference between the cathode and reference electrodes, 14 and 20 respectively, to match the sum of the two set points 50 and 36. Thus, the aforementioned differential voltage may be at some threshold value with respect to the DC set point 50. The modulation set point 36 may be then adjusted to cause the differential voltage to alternate between the threshold voltage and some more negative voltage which exceeds the reduction potential desired. The current to the cathode of the cell 10 produces a voltage across the series resistor 56 which is then amplified by demodulation differential amplifier 66. The changes in current caused by the modulator circuit 16 is amplified by the AC coupled amplifier 33 and eliminates the DC component. The AC signal voltage from the amplifier 33 is demodulated by means of a logic circuit 40 which contains a delay circuit for the purpose of excluding the transient spikes, shown in FIG. 4 in the region A, in the signal wave form from the demodulator 18 output by delaying the demodulating switching voltage until the transient spikes generated in the cell 10 have decayed.

While there has been described and illustrated specific embodiments of the invention, it will be obvious that various changes, modifications and additions can be made herein without departing from the field of the invention which should be limited only by the scope of the appended claims.

Having thus fully described the invention, what is claimed as new and desired to be secured by Letters Patent of the United States is:

1. An apparatus for providing specificity in an electrochemical analytical device and for continuous determination of a nitroglycerin concentration in a sample solution which comprises:
    a three element electrochemical cell having a grounded anode, a calomel reference electrode and a cathode electrode;
    modulator circuit means, electrically coupled to said electrochemical cell, for supplying a square wave modulated negative potential signal to said cathode electrode;
    demodulator circuit means, electrically coupled to said modulator means, for measuring the difference in the cell current of said electrochemical cell between said cathoe electrode and said anode electrode at the part and finish of said square wave modulated negative potential signal pulse and for generating an output signal proportional to said nitroglycerin concentration;
    gating circuit means, electrically connected to said modulator and demodulator means, for supplying a continuous pulse signal to said modulator means and for controlling said demodulator means to allow only the cell current generated by the reduction of said nitroglycerin concentration to pass through said gating means, and to allow substantially all switching current transients generated in said electrochemical cell to decay,
    inverter-amplifier means electrically coupled to said gating means for filtering and amplifying said cell current passed by said gating means; and
    indicator means electrically connected to said amplifier means for providing an output signal proportional to said nitroglycerin concentration in said sample solution.

2. An apparatus as recited in claim 1 wherein said modulator circuit means comprises:
    a proportional and reset controller having a plurality of input terminals and an output terminal;
    a DC set point supply having an output electrically connected to a first input of said plurality of input terminals of said controller, said DC set point supply providing a DC voltage for said cathode electrode of said electrochemical cell;
    a modulation set point supply having an output electrically coupled to a second input of said plurality of input terminals of said controller providing a square wave signal to said cathode electrode of said electrochemical ceil;
    a first differential amplifier having an output electrically connected to a third input of said plurality of input terminals of said controller, a first input electrically connected to said calomel reference electrode, and a second input electrically coupled to said cathode electrode; and a series adjustable resistor electrically coupled intermediate said controller output terminal and said cathode electrode;

wherein the cathode voltage generated at said cathode electrode is compared by said first differential amplifier to the voltage generated at said reference electrode and said controller sums the difference voltage from the output of said first differential amplifier with the output from said DC set point supply, and with a square wave output voltage from said modulation set point supply, said controller output drives said reference cell cathode electrode through said adjustable series resistor so that the sum of the voltages seen by said controller is zero, thereby making said electrochemical cell cathode voltage assume a value such that the difference between the voltages of said cathode and reference electrodes is a linear function of the sum of said DC and AC set point supply voltages.

3. An apparatus as recited in claim 1 wherein said demodulator circuit comprises:
a second differential amplifier having an input electrically connected across said series adjustable resistor and having an output signal proportional to the sum of the DC and AC component voltages generated across said series adjustable resistor;
an AC amplifier having an input electrically coupled to the output of said second differential amplifier, said AC amplifier providing an amplified AC output therefrom which does not include the DC components impressed on the input of said AC amplifier; and
an inverter-amplifier electrically connected to the output of said AC amplifier, said inverter-amplifier having a gain-of-one and generating a DC output signal therefrom.

4. An apparatus as recited in claim 1 wherein said gating circuit means comprises:
an electric clock module having a square wave 60 Hz signal output pulse;
a counter having an input electrically connected to the output of said clock module, said counter having a 5 Hz symmetrically shaped square wave modulated output pulse which is electrically coupled to the input of said modulation set point supply;
logic circuit means having an input electrically connected to the output of said counter and an unsymmetrical first and second logic output signal, said first output signal being delayed by a time Td and said second output signal being delayed by a time, Td + (t/2), where T is the period of said modulated output pulse; and
a first analog gate having an input electrically connected to said first output signal of said logic circuit and an output; and
a second analog gate having an input electrically connected to said second output signal of said logic circuit and to the output of said AC amplifier, and an output electrically coupled to the output of said first analog gate, said first and second analog gates remaining cut off for a relatively short period to allow substantially all switching current transients generated in said electrochemical cell to decay.

5. An apparatus as recited in claim 1 wherein said indicator means comprises a digital meter.

6. An apparatus as recited in claim 1 wherein said indicator means comprises a recorder.

7. An apparatus as recited in claim 1 wherein said indicator means comprises an alarm means.

8. An apparatus as recited in claim 1 wherein said indicator means comprises a digital meter electrically in parallel with a recorder and an alarm means.

* * * * *